(12) United States Patent
Kreidler

(10) Patent No.: US 8,518,338 B2
(45) Date of Patent: Aug. 27, 2013

(54) STERILIZATION CONTAINER WITH FILTER UNIT

(75) Inventor: Winfried Kreidler, Tuttlingen (DE)

(73) Assignee: Innovations-Medical GmbH, Tuttlingen (DE)

( * ) Notice: Subject to any disclaimer, the term of this patent is extended or adjusted under 35 U.S.C. 154(b) by 0 days.

(21) Appl. No.: 13/354,890

(22) Filed: Jan. 20, 2012

(65) Prior Publication Data

US 2012/0189508 A1    Jul. 26, 2012

(30) Foreign Application Priority Data

Jan. 21, 2011  (DE) .................... 20 2011 001 772 U

(51) Int. Cl.
*A61L 2/20* (2006.01)
*B65D 39/08* (2006.01)

(52) U.S. Cl.
USPC .......................... 422/291; 220/293; 422/292

(58) Field of Classification Search
USPC ................................................. 220/296, 796
See application file for complete search history.

(56) References Cited

U.S. PATENT DOCUMENTS 3,860,133 A * 1/1975 Boxer et al. .................. 215/206
4,783,321 A   11/1988 Spence
5,324,489 A    6/1994 Nichols et al.

FOREIGN PATENT DOCUMENTS

DE   10 2008 053 301 A1   4/2010
DE      202010001382 U1    4/2010
DE   20 2010 009 925 U1   10/2010

OTHER PUBLICATIONS

English translation of DE 202010001382, Gottfried Storz Medizintechnik, Apr. 2010.*

* cited by examiner

*Primary Examiner* — Sean E Conley
*Assistant Examiner* — Donald Spamer
(74) *Attorney, Agent, or Firm* — McGlew and Tuttle, P.C.

(57) ABSTRACT

A sterilization container has a box-like lower part and a removable container cover (1), which form a closed, airtight sterilization space. Ventilating openings (4), through which exchange of air takes place between the sterilization space and the environment, are provided in a wall area (2) of the sterilization container. A cover plate (6) detachably meshes with the wall area (2) through at least one spring-loaded snap-in or locking connection (9). The cover plate (6), as a round disk with a peripheral ring wall, has on the outside a peripheral locking groove, which detachably meshes with a plurality of locking elements (9) arranged in the peripheral area of the cover plate (6). The locking elements (9) are arranged stationarily as a separate assembly unit each in mounting holes of ring segments (8) projecting axially over the wall area (2), which mounting holes extend at right angles to the cover plate (6).

20 Claims, 7 Drawing Sheets

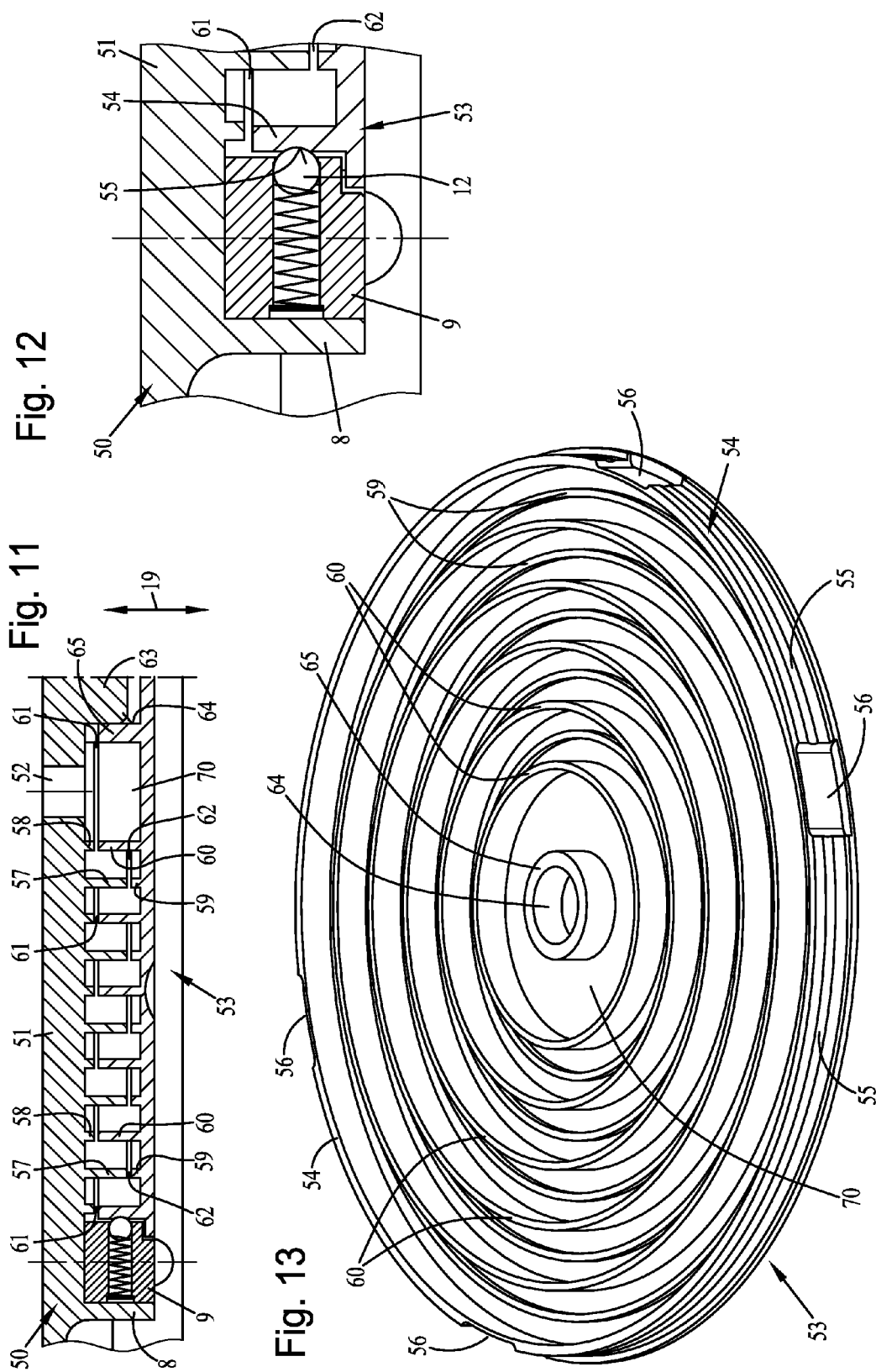

STERILIZATION CONTAINER WITH FILTER UNIT

CROSS REFERENCE TO RELATED APPLICATIONS

This application claims the benefit of priority under 35 U.S.C. §119 of German Utility Model DE 20 2011 001 772.9 filed Jan. 21, 2011, the entire contents of which are incorporated herein by reference.

FIELD OF THE INVENTION

The present invention pertains to a sterilization container comprising a box-like lower part and a removable container cover, which form a closed, airtight sterilization space, wherein ventilating holes, through which exchange of air takes place between the sterilization space and the environment in the closed state, are provided in a wall area of the sterilization container, and wherein the wall area is part of a sterilization barrier, which brings about sterilization of the air entering the sterilization space through the ventilating openings, in the area of the ventilating openings together with a cover plate, wherein the cover plate detachably meshes with the wall area through at least one spring-loaded snap-in or locking connection.

BACKGROUND OF THE INVENTION

Sterilization containers with a lower housing as well as a tightly attachable container cover have already been known for a long time and are used, for example, to sterilize medical devices. To guarantee ventilation and removal of air with the sterilization container closed, such sterilization containers are provided, in at least one of their wall areas, with gas exchange openings, which may be covered, for example, by means of a filter blade on the inside during the operation. As such a filter blade is to be replaced as the operating time increases, such a filter blade is held replaceably by means of a pressing disk on the side on the wall area. The pressing disk is correspondingly arranged on the inside on the wall area and detachably meshes with a frame element surrounding the gas exchange openings in a ring-shaped pattern. This detachable connection between the pressing disk and frame element can be established here by a bayonet connection, which is formed from bayonet catch elements or bayonet connection elements, which can be caused to mutually mesh with one another, on the pressing disk, on the one hand, and on the frame element, on the other hand. At least one sealing ring is provided to seal the pressing disk against the corresponding wall area of the sterilization container and against the frame element. This sealing ring is received on the wall side in a peripheral annular groove of the pressing disk or of the cover plate. To achieve good sealing action, this sealing ring presses in the mounted state the filter blade, which is inserted, in a relatively accurately fitting manner, into the ring-shaped frame element. The pressure disk thus forms, together with the filter blade and frame element, a kind of filter unit.

Based on the bayonet connection provided between the pressing disk and frame element, the pressing disk can be detached from the frame element and reinserted into same only by a relative rotary motion. Since the sealing ring of the pressing disk sealingly presses the filter blade, and the pressing disk can be correspondingly braced under an axial prestress against the filter blade, this relative rotary motion leads, especially during the mounting of the pressing disk, to a displacement of the filter blade and/or to damage thereto.

It would therefore be extremely advantageous to replace this bayonet connection by another type of connection in order to avoid such a destruction or displacement of the filter blade.

A sterilization container, which likewise comprises a box-like lower part and a container cover, which can be placed tightly on the lower part, is known in this connection from DE 20 2010 001 382 U1. However, instead of a filter blade, a so-called Pasteur loop is provided as the filter unit in this sterilization container. Such a Pasteur loop comprises, as a rule, two plates, namely, a base plate and a cover plate, which have concentric annular ribs each. These annular ribs of the base plate and of the cover plate mesh with one another with a radial clearance axially such that both axial and radial annular gaps are formed. Furthermore, a wall section of the container cover is provided in the area of this Pasteur loop with ventilation openings, through which ventilation and removal of air from the closed sterilization container take place during the operation. The air, which enters through the ventilation openings and flows through these annular gaps alternatingly radially and axially and finally enters the sterilization space and leaves the latter, is sterilized by the Pasteur loop.

The base plate, which is mounted on the wall element of the container cover on the inside by means of screw connections or the like, is designed as a complete, separate component with its annular ribs in the subject of DE 20 2010 001 381 U1. In one embodiment variant, the cover plate can be caused to lockingly mesh with the base plate by means of a plurality of spring-loaded locking balls distributed uniformly over the circumference. These locking balls are arranged here in an axially projecting, peripheral retaining ring, which surrounds the cover plate. Due to the base plate being designed as a separate component, it is possible to prepare, in particular, the cross holes for receiving the locking balls as well as the axial compression springs loading these in an extremely simple manner. However, it was found that it is absolutely necessary for this to design this base plate as a separate component and to prepare the corresponding cross holes in the edge web and to insert the locking balls before mounting. It is only thereafter that the base plate can be placed on the inside on the wall section of the container cover with the ventilating openings thereof. This special construction of the locking connection would also be able to be used to fix a filter blade. However, separate design of the base plate is always necessary here to make it possible to prepare the cross holes in the edge web.

SUMMARY OF THE INVENTION

Accordingly, a basic object of the present invention is to design a locking connection for mounting the cover plate such that the base plate is a one-piece, integral part of the corresponding wall section with the ventilating openings hereof.

This object is accomplished according to the present invention with a sterilization container comprising a box-like lower part and a removable container cover, which form a closed, airtight sterilization space, wherein ventilating openings, through which an exchange of air takes place between the sterilization space and the environment in the closed state, are provided in a wall area of the sterilization container, and wherein the wall area is part of a sterilization barrier, which brings about sterilization of the air entering the sterilization space through the ventilation openings, in the area of the ventilating openings together with a cover plate. The cover plate detachably meshes with the wall area through at least one spring-loaded snap-in or locking connection. The cover plate is designed as a round disk with a peripheral ring wall, which has on the outside a peripheral locking groove, which detachably meshes with a plurality of locking elements arranged in the peripheral area of the cover plate. The locking elements are arranged as separate assembly units each stationarily in ring segments, which are arranged stationarily in mounting holes of ring segments projecting axially over the wall area, which mounting holes extend at right angles to the cover plate.

Due to the design according to the present invention, an additional base plate for accommodating or arranging the locking elements can be eliminated. Thus, a plurality of dome-shaped projections or ring segments, which are arranged on a circular path and which are provided with axial mounting holes or mounting holes extending at right angles to the wall element, are provided on the bottom of the container or at the wall element of the sterilization container. A locking element comprising a plurality of parts can be inserted stationarily into these mounting holes. By selecting the arrangement of these ring segments correspondingly, a cover plate can thus be positioned accurately and locked on the inside in the corresponding wall area of the sterilization container without any rotary motion whatsoever.

The ring segments with their locking elements may also be part of the cover plate according to the present invention. The annular groove is located in such a case in a peripheral ring web of the corresponding wall area, which said ring web encloses the cover plate.

The combinations of the features of the housing blocks pertain to especially advantageous variants of the locking element.

Thus, provisions may be made for the locking elements to comprise a more or less cylindrical housing block each, which is provided with a transversely extending radial hole, in which a locking ball, which partially projects radially from the housing block and meshes with the locking groove in the mounted state, is arranged, and for the locking ball to be held elastically and non-rigidly in its meshed position by an axial compression spring arranged in the radial hole.

Provisions may be made for the radial hole to have, in the area of the partially radially projecting locking ball, an inwardly directed stop web, by which the maximum radial projection of the locking ball is determined.

Furthermore, the radial hole of the housing block may be provided in its end area located opposite the locking ball, with a closing plate, which is accommodated stationarily in a milled recess of the housing block and at which the axial compression spring is axially supported.

In a variant of the present invention, the filter unit of the sterilization container may have a filter blade covering the ventilating openings on the inside between the cover plate and the wall area of the container cover. The locking connection between the cover plate and wall area brings about a clamping force, with which the filter blade is pressed against the wall area of the container cover. A filter blade covering the ventilating openings on the inside is provided between the cover plate and the wall area of the container cover.

For such an embodiment, the cover plate may have, in particular, a radially projecting grip part, which is arranged between two adjacent ring segments of the cover plate in the mounted state, wherein the grip part is located at a spaced location from the inner surface of the cover wall of the container cover. A locking connection existing between the cover plate and the locking elements can be abolished by this grip part in a simple manner by manually raising the grip part and hence the entire cover plate. Due to the distance between the grip part and the inner surface of the cover wall, the grip part can be securely grasped manually. Due to the grip part provided, a relative rotation of the cover plate relative to the inserted filter blade is not necessary to abolish the locking connection, so that the filter blade cannot be damaged, especially for its possible further use.

To securely "grip behind" the grip part with the fingers, the grip part may have, in addition to this embodiment, a bevel on its "underside" located towards the surface of the container cover, and the distance from the surface of the container bottom is greater in the radially outer end area of said grip part than in the radially inner area thereof.

The filter unit and hence the sterilization barrier may comprise, as an alternative to the embodiment according discussed with the filter blade, a Pasteur loop. This Pasteur loop is formed from ring webs of the area, which mutually mesh with one another axially in the radial direction, on the one hand, and from the cover plate, on the other hand. Since no filter blade is provided here, the cover plate can be rotated relative to the wall area, because destruction of such a filter blade is not to be feared. An alternative embodiment to the separation of the locking connection is correspondingly provided here. Thus, the locking groove may be interrupted by a plurality of recesses, whose number and arrangement correspond to the number and arrangement of the locking elements, the recesses being open starting from the locking groove towards the wall area of the container cover.

The locking connection can be abolished by lifting off the cover plate in this embodiment as well. To abolish the locking connection in a simpler manner, provisions may be made for the cover plate to be rotatable relative to the wall area of the container cover and for the recesses to overlap the locking elements arranged in the peripheral area of the cover plate and to be able to be disengaged from the locking groove by correspondingly setting the relative angular position of the cover plate in relation to the wall area.

To facilitate the setting of this relative angular position of the cover plate in relation to the container cover, marks may be provided in the peripheral area of the cover plate on the container cover and in the edge area of the cover plate, which said marks are arranged radially aligned with one another if the locking elements are located in the peripheral area of the respective associated recess.

To mount the cover plate in the correct position, the wall area of the sterilization container may have a central mounting pin projecting towards the cover plate, on which the cover plate is received in the mounted state with a mounting hole concentrically with the ring segments in the wall area, which said ring segments are arranged on the circumference.

If an embodiment of the cover plate without radially projecting grip part is provided, the distance between adjacent locking elements may be selected to be such that the cover plate can be grasped between them manually at its circumference. The cover plate can thus be "pulled off" or "lifted off" in a simple manner in such an embodiment.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 11 is a vertical partial section of the wall section from FIG. 10 with inserted cover plate;

FIG. 12 is an enlarged detail from FIG. 11 in the area of the ring segment with an inserted locking element; and FIG. 13 is a perspective view of a cover plate provided with ring webs.

DESCRIPTION OF THE PREFERRED EMBODIMENTS

Figure 1:
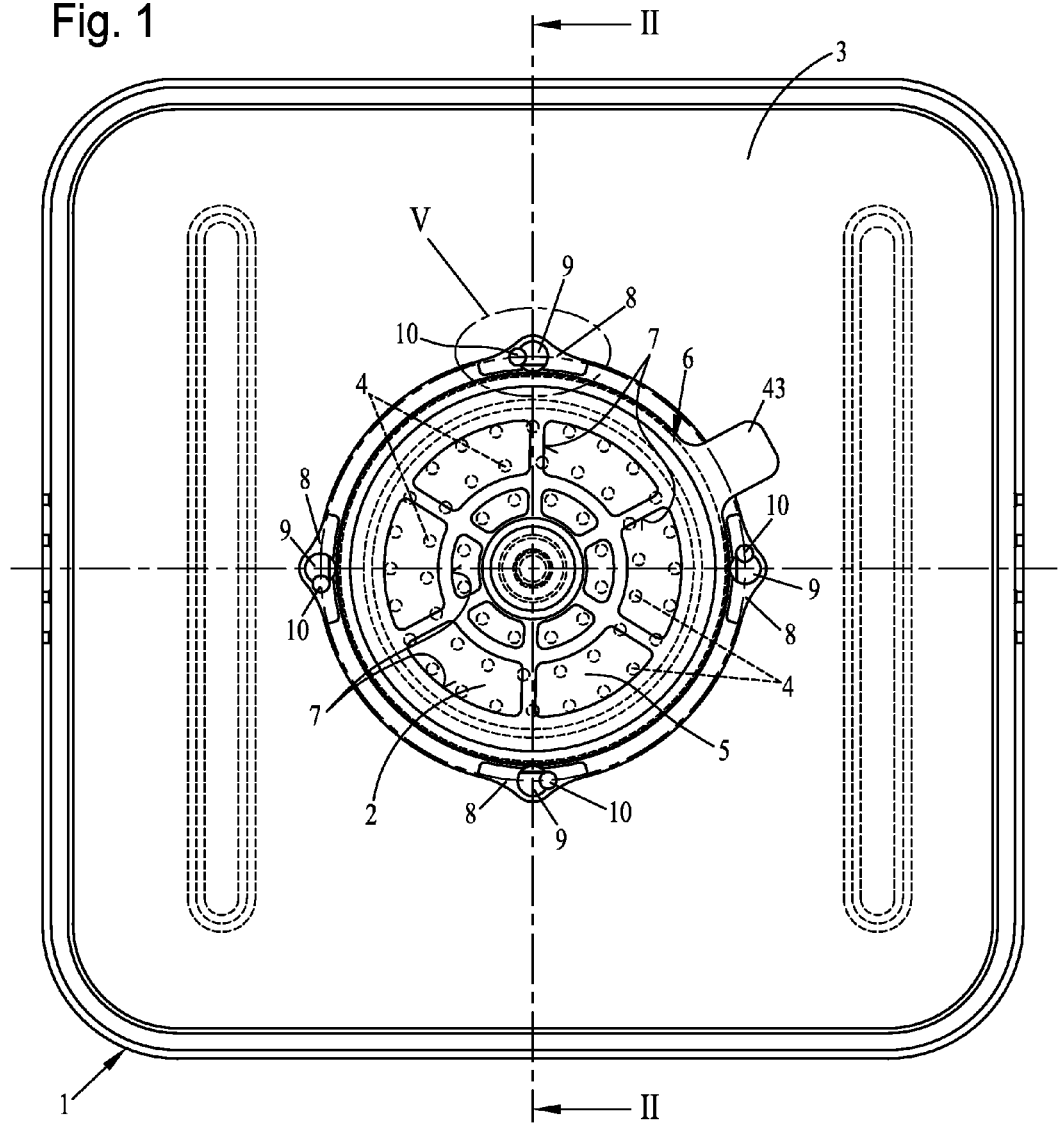
FIG. 1 is an inner view of a container cover of the sterilization container of FIG. 1a, in which a plurality of ventilating openings are provided in a wall area and the filter unit has a filter blade.
Figure 1A:
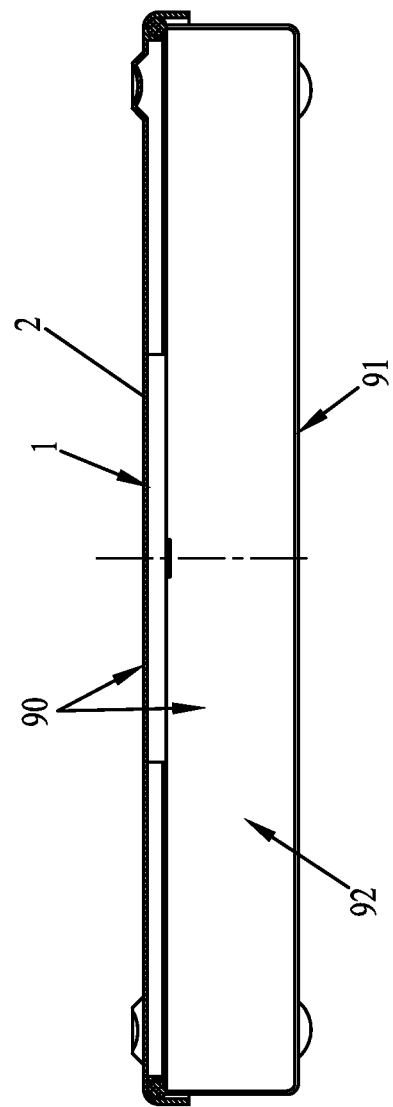
FIG. 1a is a schematic sectional view of a sterilization container with a box-like lower part and with an attached container cover.

Referring to the drawings in particular, a sterilization container 90 shown schematically in FIG. 1*a* comprises a box-like lower part 91 and a detachable container cover 1, which form a closed, air-tight sterilization space 92, wherein ventilation openings 4 (FIG. 1), through which exchange of air takes place between the sterilization space 92 and the environment in the closed state, are provided in a wall area 2 of the sterilization container 90.

FIG. 1 shows an inner view of the container cover 1 from FIG. 1*a*, which can be tightly attached to the lower part 91 of the sterilization container 90 (FIG. 1*a*), as this is sufficiently known from the state of the art. On the embodiment variant shown, the container cover 1 has a plurality of ventilating openings 4, which are covered by a filter blade 5 on the inside, in a central wall area 2 of its cover wall 3. Since this filter blade 5 covers the ventilating openings 4, the ventilating openings 4 are indicated by broken lines in FIG. 1.

A cover plate 6 designed as a circular disk, which has a plurality of large-area openings 7, is provided to fix the filter blade 5 in the embodiment variant being shown. The wall area 2 with its ventilating openings 4 thus forms, together with the filter blade 5 and the attached cover plate 6, a kind of sterilization barrier, via which an inner sterilization space of a sterilization container (not shown in the drawing) is ventilated and evacuated during the operation, in the embodiment variant being shown.

Figure 2:
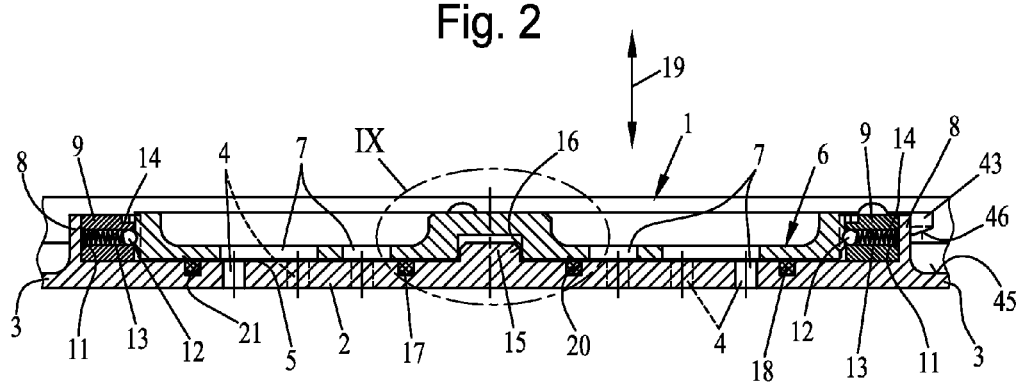
FIG. 2 is a partial sectional view along line II-II of the container cover from FIG. 1.

Furthermore, FIG. 1 shows that a plurality of ring segments 8, which each extend over a part of the circumference of the cover plate 6, are provided in the peripheral area of the cover plate 6. Each of these ring segments 8 is provided with a locking element 9, which is held stationarily in the respective associated ring segment 8 by means of a spring-type straight pin each. FIG. 2 shows for this a partial vertical section II-II from FIG. 1 of the container cover 1 with the wall area 2 thereof and with the cover plate 6 placed on the inside.

As is apparent from FIG. 2, the ring segments 8 are arranged radially outside the cover plate 6 in the peripheral area thereof. Each ring segment 8 has a mounting hole 11, into which the respective associated locking element 9 is stationarily inserted. It can be recognized from FIG. 2 as a suggestion that each locking element 9 is provided with a locking ball 12 as well as with an axial compression spring 13, which are correspondingly inserted into a radial hole 14 of the respective locking element 9. The cover element 6 is held lockingly on the inside on the wall area 2 and cover wall 3 of the container cover 1 by means of this locking ball 12. To accurately position the cover plate 6 between the ring segments 8, the wall area 2 forms on the inside a central mounting pin 15, which correspondingly meshes with a mounting hole 16 of the cover plate 6, which mounting hole 16 is designed as a blind hole, in a positive-locking manner.

Furthermore, FIG. 2 shows the filter blade 5 as a suggestion. Respective O-rings 17 and 18, which are pressed on the underside sealingly against the filter blade 5 under an axial prestress in the direction of the double arrow 19 in the state shown in FIG. 2, in which the cover plate 6 is mounted on the wall area 2, are provided to seal this filter blade 5 both radially inwardly towards the mounting ring 15 and radially outwardly towards the ring segments 8. The two O-rings 17 and 18 are correspondingly inserted into a respective peripheral mounting groove 20 and 21 of the wall area 2.

Figure 3:
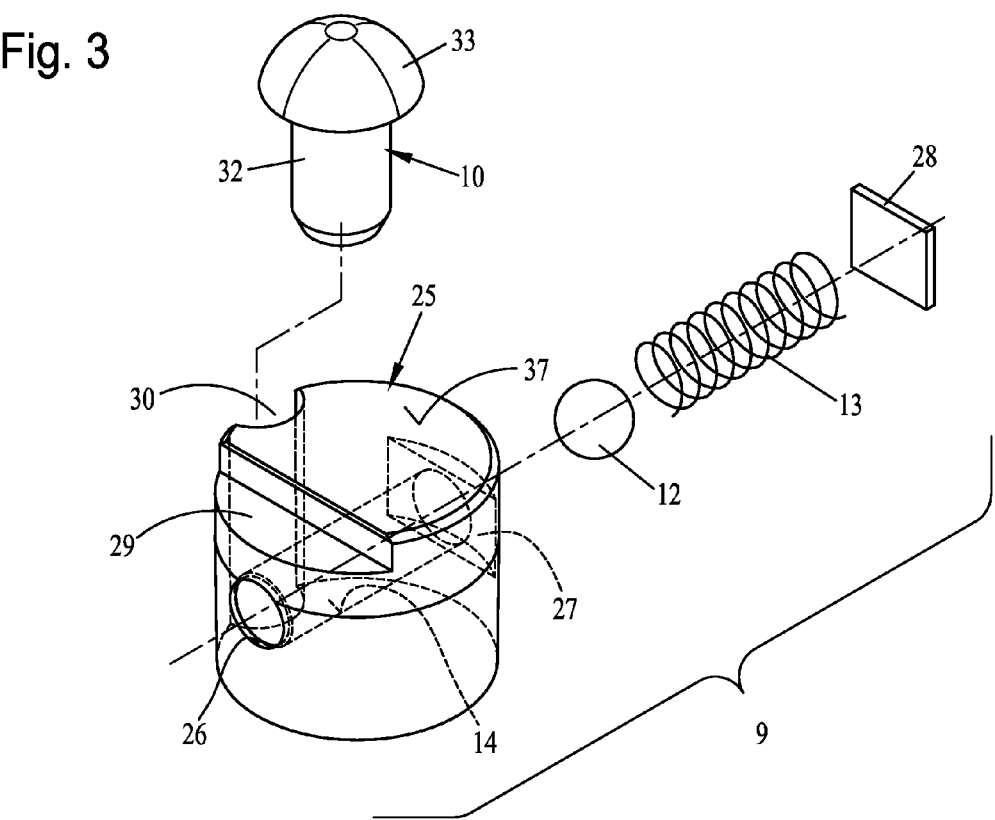
FIG. 3 is a perspective exploded view of a possible embodiment variant of a locking element.

The ring segments 8 shown in FIG. 1 with their locking elements 9 are of an identical design in this exemplary embodiment, and the individual components of the locking elements are shown as an example in a perspective exploded view in FIG. 3.

In the embodiment variant being shown, locking element 9 comprises a central, essentially cylindrical housing block 25, which has the radial hole 14 already mentioned in connection with FIG. 2 to mount the locking ball 12 as well as the axial compression spring 13. This radial hole 14 is arranged approximately at half the height of the housing block 25. The radial hole 14 forms in its left-hand end area a radially inwardly projecting stop web 26, whose diameter is made smaller than the diameter of the locking ball 12. It is thus achieved that the locking ball 12 protrudes radially from the housing block 25 by a predetermined amount in this end area, but cannot be pushed out of the radial hole 14.

In the end area of the radial hole 14, which end area is located axially opposite this stop web 26, the housing block 25 is provided with a flat milled area 27, into which a closing plate 28 can be placed stationarily. This closing plate 28 can be fixed by a pressed connection or even by a laser welded connection. The axial compression spring 13 is axially prestressed in the mounted state by this closing plate 28 and is supported axially at the closing plate 28, so that the locking ball 12 is pressed with a predefined axial force against the stop web 26 of the mounting hole 11.

Figure 4:
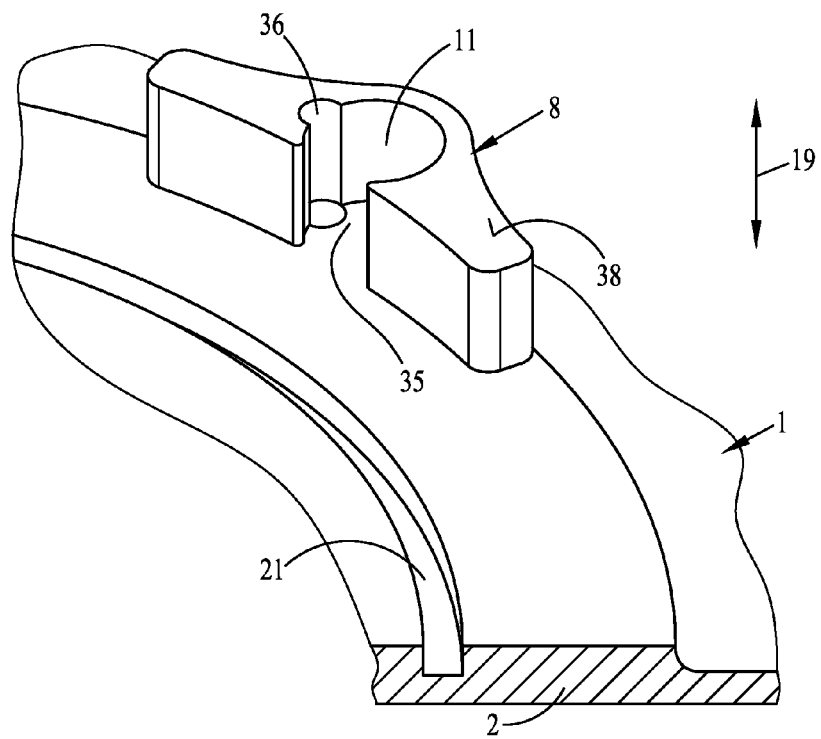
FIG. 4 is a perspective view of a ring segment, which axially projects on the inside over the wall section of the container cover and is used to receive the locking element from FIG. 3.

Furthermore, it can be recognized from FIG. 3 that the housing block 25 has, on the top side, in the area of the stop web 26, another milled area 29, into which, for example, a radially minimally projecting collar web of a cover plate can protrude. In a rear, lateral area, housing block 25 has a partially cylindrical milled area 30, into which the spring-type straight pin 10 recognizable in FIG. 1 can be inserted. This spring-type straight pin is used to stationarily mount the locking element 9 in the ring element 8 shown in a perspective view in FIG. 4. The spring-type straight pin 10 correspondingly forms a clamping spigot 32 as well as a head part 33.

As was already mentioned above, FIG. 4 shows a perspective view of one of the ring segments 8, which is placed on the top side on the wall area 2 of the container cover 1 or is made integrally in one piece with same. Furthermore, the radially outer mounting groove 21 of the wall area 2 can also be recognized in FIG. 4. In the embodiment variant of the container cover 1 being shown, this wall area 2 is elevated in the manner of a platform. However, this is not absolutely necessary. It can, furthermore, be recognized from FIG. 4 that the ring segment 8 has a kind of mounting hole 11, which forms an opening 35 extending over the full height of the ring segment 8 towards the mounting groove 21. The locking element 9 from FIG. 3 with its housing block 25 can be fittingly inserted into this mounting hole 11. To fix this housing block 25 in the mounting hole 11 by means of the spring-type straight pin 10, mounting hole 11 likewise has in its edge area a partially cylindrical hole section 36, which forms a fully peripheral cylindrical hole in the mounting hole 11 together with the milled area 30 of the housing block 25 in the state in which the housing block 25 is mounted in the mounting hole 11.

The housing block 25 is thus held, on the one hand, stationarily in the mounting hole 11 in the mounted state by the spring-type straight pin 10, and, on the other hand, radial alignment of the radial hole 14 to the mounted cover plate 6 is achieved due to the defined arrangement of the milled area 30 on the circumference of the housing block 25 and the defined arrangement of the hole section 36 on the circumference of the mounting hole 11, so that the locking ball 12 also points radially inwardly in the mounted state, as this can be recognized especially from FIGS. 1 and 2.

In the shown embodiment variant of the ring segment 8 and of the locking element 9, these are of equal length in their axial extensions indicated by the double arrow 19, so that the housing block 25 ends with its surface 37 flush with the surface 38 of the ring segment 8 in the mounted state. Due to the locking element 9 being designed as a separate component, this can be manufactured in an extremely simple manner. In particular, it is not necessary to provide a radial hole in the segment 8, for example, in the area of the mounting hole 11, in order to make it possible to insert the locking ball 12 there together with the axial compression spring 13 as well as the closing plate 28. This ring segment 8 can consequently also be a one-piece part of the wall area 2 or of the container cover 1.

Figure 6:
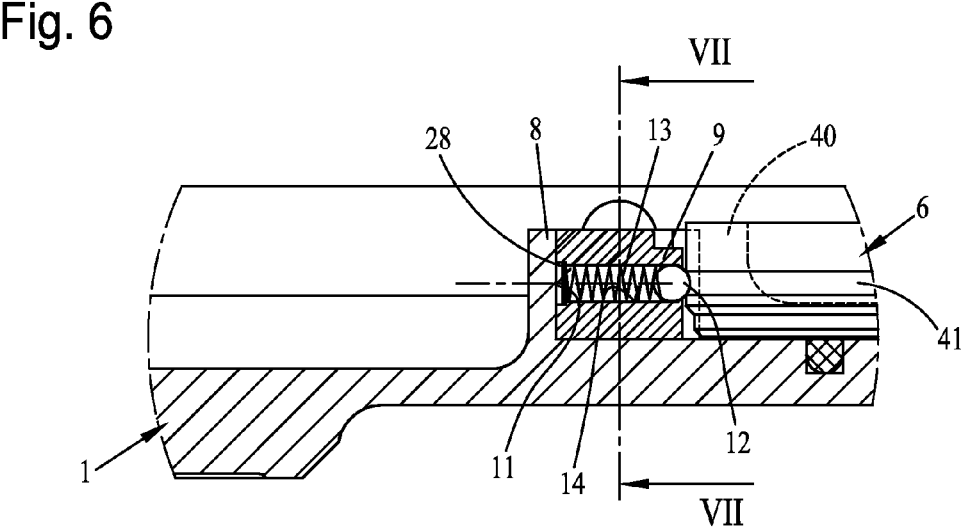
FIG. 6 is a sectional view taken along line VI-VI of the ring segment from FIG. 5 with inserted locking element.

Furthermore, it can be recognized from FIG. 1 in this connection that the cover plate 6 can be inserted with extremely small clearance between the ring segments 8, of which four are provided in this embodiment variant. To hold the cover plate 6 with sufficient holding force on the filter blade 5, cover plate 6 has a vertically upwardly directed, peripheral ring wall 40 (FIG. 6), which is provided with a peripheral locking groove 41.

Figure 5:
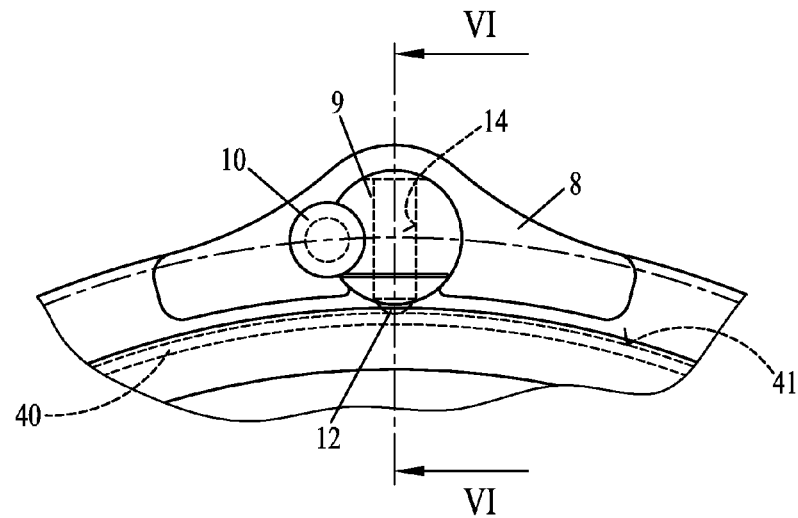
FIG. 5 is an enlarged detail V of a ring segment from FIG. 1 with an inserted locking element from FIG. 3.

FIG. 5 shows for this as an example a ring segment 8, into which locking element 9 is stationarily inserted. This locking element 9 is held stationarily in ring segment 8 via the spring-type straight pin 10. Due to the corresponding peripheral arrangement of both the milled area 30 (FIG. 3) and the hole section 36 (FIG. 4), the radial hole 14 of the locking element 9 is aligned radially, so that the locking ball 12 meshes with the peripheral locking groove 41 in the mounted state. This can also be recognized especially from the sectional view in FIG. 6. The radial hole 14 is closed in this mounted state of the locking element 9 in the mounting hole 11 of ring segment 8 by means of the closing plate 28, so that the axial compression spring 13 presses the locking ball 12 into the locking groove 41 of ring wall 40 of the cover plate 6.

Figure 7:
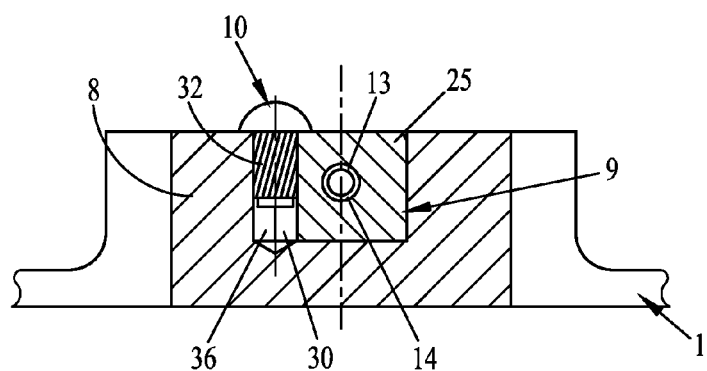
FIG. 7 is a sectional view taken along line VII-VII from FIG. 6.

It can be recognized from the sectional view shown in FIG. 7 that milled area 30 and hole section 36 together form a uniform mounting hole of the clamping spigot 32 of the spring-type straight pin 10. The diameter of clamping spigot 32 may be made minimally greater than the diameter of the hole formed from the milled area 30 and hole section 36, so that the housing block 25 of locking element 9 is held stationarily in mounting hole 11 of ring segment 8. The axial compression spring 13 in the radial hole 14 of housing block 25 can also be recognized from FIG. 7.

Figure 8:
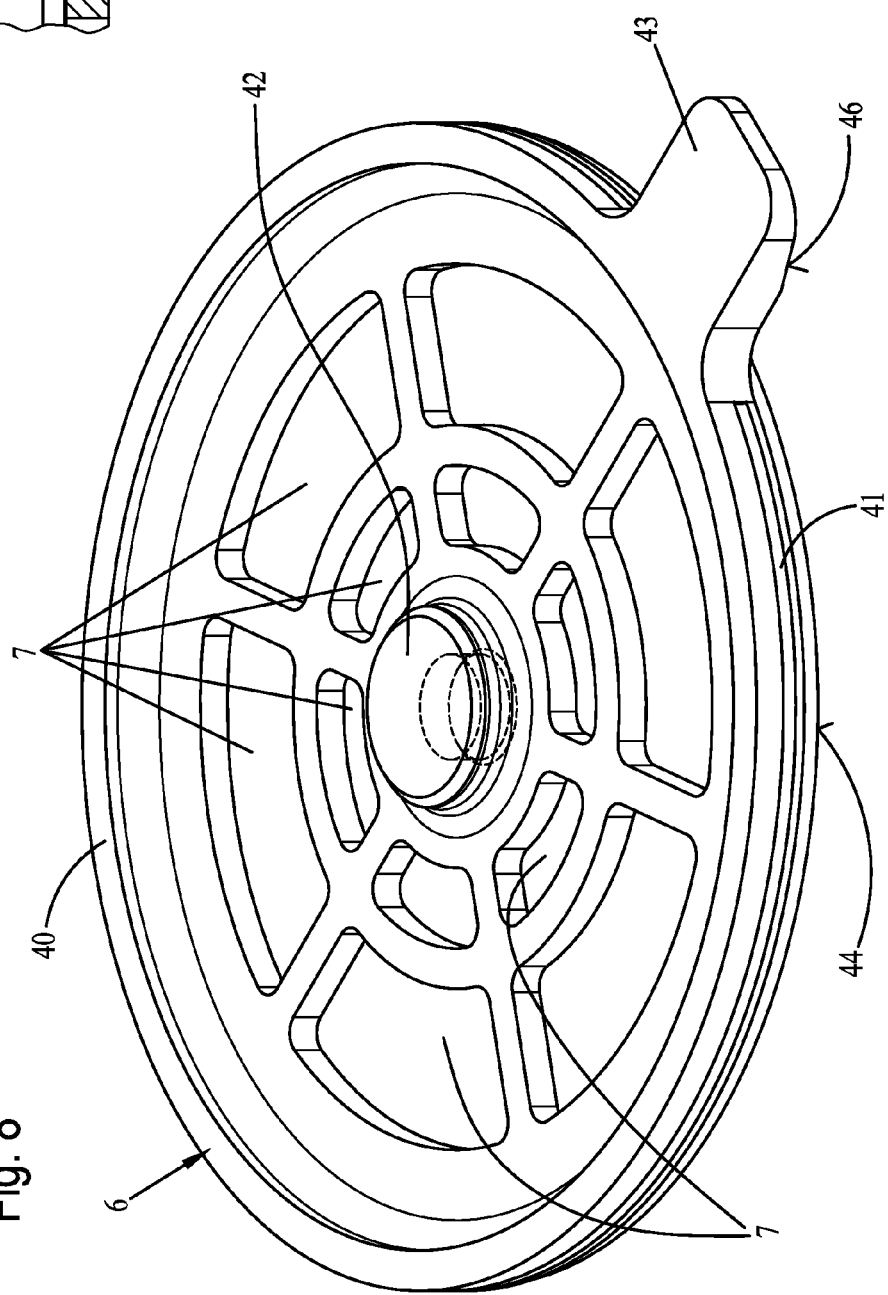
FIG. 8 is a perspective view of the cover plate used in the filter unit from FIG. 1.

FIG. 8 shows a perspective view of the pressing plate 6 from FIG. 1. FIG. 8 shows the peripheral ring wall 40 with the at least partly peripheral locking groove 41. FIG. 8 also shows the large-area openings 7. In the center, cover plate 6 forms a pin-like elevation 42, in the area of which the mounting hole 16 (FIG. 9) already mentioned in connection with FIG. 2 is provided on the underside.

Furthermore, it can be recognized from FIG. 2 that the cover plate 6 is provided in the exemplary embodiment being shown with a radially outwardly projecting, plate-like grip part 43 at its peripheral ring web 40. This grip part 43 has a vertical distance from the lower support surface 44 of cover plate 6, so that in the state in which the cover plate 6 is mounted on wall section 2, grip part 43 has a distance from the surface 45 of the cover wall 3, as this can be recognized as a suggestion from FIG. 2. To make it possible to grasp behind the grip part 43 with the fingers more easily, grip part 43 has a "lower" bevel 46 towards its radially outer end, as a result of which the distance from surface 45 of the cover wall 3 is increased. The cover plate 6 can be released from the locking connection between the locking balls 12 and locking groove 41 in a substantially simpler manner from its locked state shown in FIG. 2 by means of this grip part 43.

Figure 9:
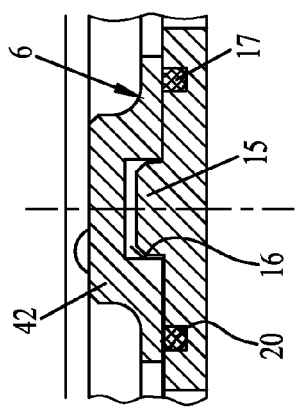
FIG. 9 is an enlarged detail IX of the mounting of the cover plate from FIG. 2 in the wall area of the container wall of the container cover from FIG. 1.

FIG. 9 shows, furthermore, the mounting area of the cover plate 6 on the wall section 2 in an enlarged view. On the one hand, the vertically upwardly projecting elevation 42 can be recognized, in the area of which the mounting hole 16 of cover plate 6 is arranged. Mounting pin 15 of the wall area 2 fittingly meshes with this mounting hole 16. Furthermore, FIG. 9 also shows the inner O-ring 17, which is correspondingly inserted into mounting groove 20. Due to the mounting pin 15 and mounting hole 16, cover plate 6 can be positioned on the wall area 2 and in the container cover 1 in a relatively accurate position. Cover plate 6 is correspondingly also held uniformly stationarily at the circumference on the container cover 1 and in the container cover 1 by means of the locking elements 9.

Instead of such a grip part 43 for removing the cover plate 6 from the wall area 2 of the container cover 1 or in addition thereto, the peripheral groove 41 may also be designed as an interrupted groove.

Figure 10:
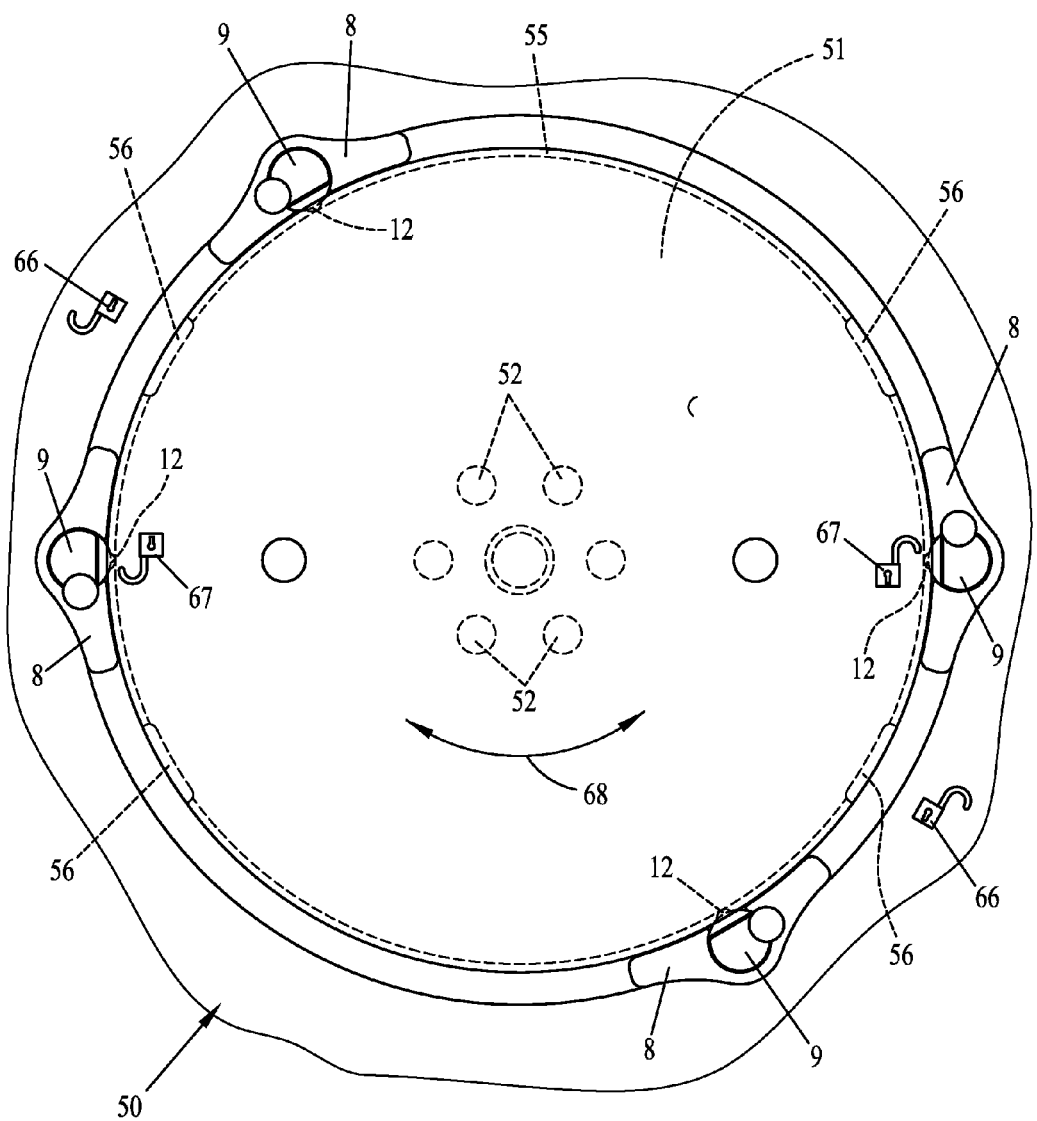
FIG. 10 is a partial top view of the inside of a wall section of a container cover, in which a Pasteur loop is used as a filter unit.

FIG. 10 shows in this connection a top view of another variant of a container cover 50 in an inner view, which forms centrally a wall section 51, which is provided with inner ventilating openings 52. These ventilating openings 52 are covered by means of a cover plate 53 in the embodiment variant according to FIG. 10 as well, but this cover plate 53 forms, together with correspondingly designed parts of wall section 51, a so-called Pasteur loop, whose basic design is known from the state of the art and is shown in a partial section in FIG. 12.

As can be recognized from FIG. 10, cover plate 53 has no outwardly projecting grip part. This cover plate 53 forms a peripheral outer ring wall 54 (FIG. 12), which is provided with a peripheral locking groove 55 (FIG. 10). This locking groove 55, which is indicated by broken lines in FIG. 10, is interrupted by a total of four recesses 56, whose radial depth is greater than the radial depth of locking groove 55.

It can be recognized from FIG. 10 that the container cover 50 is likewise provided on the inside in this embodiment variant with four ring segments 8 of identical design, into which a locking element 9 each is likewise inserted. In this embodiment variant shown, the ring segments 8 are arranged with their locking elements 9 in pairs at different angular distances from one another in the peripheral area of the cover plate 53. The recesses 56 of the locking groove 55 are also arranged in the peripheral ring wall 54 corresponding to these distances.

In the position or angular position shown in FIG. 10, the cover plate 53 with its peripheral locking groove 55 is snapped stationarily in the locking balls 12 of the locking elements 9, which said locking balls can be recognized as a suggestion. This locking meshing is shown especially by the two partial sections in FIGS. 11 and 12. Thus, the sectional view in FIG. 11 shows one of the ring segments 8 together with a mounted locking element 9. FIG. 12 shows this part from FIG. 11 in an enlarged view. Locking ball 12 meshes in this mounted state with the peripheral locking groove 55 of the edge web 54 in a positive-locking manner. Cover plate 53 is held by this positive-locking meshing in the axial position shown in FIGS. 11 and 12 in relation to the wall section 51 of the container cover 50.

As can be recognized especially from FIG. 11, this wall section 51 of the container cover 50 has, in the area of the cover plate 53, corresponding ring webs 57 and 58, which have different heights in their axial extension indicated by double arrow 19. Corresponding to this design in terms of height, cover plate 53 likewise has corresponding ring webs 59 and 60 towards the container cover 50, which are arranged correspondingly overlappingly in terms of their diameters and their height with the ring webs 57 and 58. Based on the locking axial fixation of the cover plate 53 by the locking balls 12, cover plate 53 is held at a distance from the container cover 50 or the wall section 51 thereof, so that respective radial gaps 61 and 62 are formed between the ring webs 57 and 59 as well as 58 and 60.

The innermost radial gap 61 opens in the radially inner area into a ring chamber 70, which is in turn in connection with the ventilating openings 52, as this can be recognized from FIG. 11 for one of the ventilating openings 52. Thus, there is a labyrinth-like connection with a closed sterilization space of a sterilization container via these ventilating openings 52 and the radial ring gaps 61 and 62, as is commonly known from the state of the art. Furthermore, FIG. 11 also shows that the wall section 51 of the container cover 50 forms a central mounting pin 63, which fittingly meshes with a correspondingly associated mounting hole 64 of the cover plate 53. The cover plate 53 is thus also held via this mounting pin 63 and the mounting hole 64 in a relatively accurate position on the inside at the container cover 50 or the wall section 51 thereof.

FIG. 13 shows once again, for the sake of completeness, a perspective "top view" of the cover plate 53. On the one hand, the vertically elevated ring webs 60 as well as the ring webs 59 with a lower height, which follow each other alternatingly in the radial direction from the outside towards the inside, can be recognized in this view. The inner ring web 65, which defines the central mounting hole 64, on the one hand, and a part of the ring chamber 70, on the other hand, can also be recognized.

Furthermore, the recesses 56 mentioned already in connection with FIG. 10 can be recognized in FIG. 13. The radial depth of the recesses is greater than the depth of the peripheral annular groove 55 of the outer ring wall 54 of the cover plate 53. The locking balls 12 are correspondingly released when these recesses 56 are correspondingly aligned with the locking balls 12, so that the cover plate 53 can be lifted off from the wall section 51 of the container cover 50 without a major effort.

To facilitate the alignment of these recesses 56 with the correspondingly associated locking balls 12 and locking elements 9, corresponding marks—for example, in the form of opened U-locks 66 and 67, respectively—may be provided both in the area surrounding the cover plate 53 on the inside on the container cover 50 and on the cover plate 53. The recesses 56 can thus be caused to overlap the locking balls 12 by correspondingly rotating the cover plate 53 in one of the directions indicated by the double arrow 68 (FIG. 10). The correct angular position of the cover plate 53 is reached if the marks 67 of the cover plate 53 in the radial direction are aligned with the marks 66 of the container cover 50.

Thus, mounting in a correct locking angular position of the cover plate 53 relative to the peripherally arranged ring segments 8 with the locking elements 9 thereof can also be set by the marks 67 and 66 being brought during the attachment, for example, into the position shown in FIG. 10. These can be arranged preferably in an angular position on the cover plate 53 in which they are, for example, aligned in their radial direction with two of the ring segments 8 with the locking elements 9 thereof, as this is shown as an example in FIG. 10. This is made possible by the fact that the ring segments 8 with their locking elements are arranged in pairs at predetermined, different peripheral distances from one another.

While specific embodiments of the invention have been shown and described in detail to illustrate the application of the principles of the invention, it will be understood that the invention may be embodied otherwise without departing from such principles.

What is claimed is:

1. A sterilization container comprising:
   a lower part;
   a removable container cover, said lower part and said container cover, in a closed state, forming a closed airtight sterilization space, a wall area of the sterilization container having ventilating openings, through which an exchange of air takes place between said sterilization space and the environment in said closed state;
   a cover plate, said wall area being part of a sterilization barrier, which brings about sterilization of air entering said sterilization space through said ventilation openings, in the area of said ventilating openings together with said cover plate, said cover plate comprising a round disk with a peripheral ring wall; and
   a spring-loaded snap-in or locking connection wherein said cover plate detachably meshes with said wall area through said spring-loaded snap-in or locking connection, wherein said cover plate peripheral ring wall has an outer peripheral locking groove which detachably meshes with a plurality of locking elements arranged in the peripheral area of said cover plate and said locking elements are arranged stationarily as a separate assembly unit each in mounting holes of ring segments projecting axially over said wall area, each of said locking elements comprising a substantially cylindrical housing block, which is provided with a transversely extending radial hole, in which a locking ball is arranged, which partially projects radially from said housing block and meshes with said locking groove in the mounted state, wherein said mounting holes extend at right angles to said cover plate, each of said ring segments comprising a radial mounting opening, one of said mounting holes of one of said ring segments being in communication with said radial mounting opening.

2. A sterilization container in accordance with claim 1, wherein:
said cover plate is arranged between said wall area and said container cover, said ring segments being integrally connected to said wall area; and
said locking ball is held elastically and non-rigidly in a meshed position by an axial compression spring arranged in said radial hole.

3. A sterilization container in accordance with claim 2, further comprising:
a connecting pin, wherein said radial hole in the area of the partially radially projecting locking ball has an inwardly directed stop web, by which a maximum radial projection of said locking ball is established, each of said ring segments comprising an inner ring segment surface, said housing block of each of said locking elements having an outer housing block surface, said outer housing block surface and said inner ring segment defining a connecting pin receiving groove, at least a portion of said connecting pin being arranged in said connecting pin receiving groove, wherein said housing block is connected to said wall area via at least said connecting pin.

4. A sterilization container in accordance with claim 2, wherein said radial hole of said housing block is provided in an end area located opposite said locking ball with a closing plate, said closing plate being received stationarily in a milled area of said housing block and at which said axial compression spring is axially supported.

5. A sterilization container in accordance with claim 1, further comprising:
a filter blade covering said ventilating openings on an inside, said filter blade being provided between said cover plate and said wall area of said container cover, wherein
said locking connection between said cover plate and said wall area brings about a clamping force, with which said filter blade is pressed against said wall area of said container cover.

6. A sterilization container in accordance with claim 1, wherein:
said cover plate has a radially projecting grip part, which is arranged in amounted state between two adjacent ring segments of said cover plate; and
said grip part is at a distance from an inner surface of said cover wall of said container cover.

7. A sterilization container in accordance with claim 6, wherein on an underside of said container cover, located towards said inner surface of said container cover, said grip part has a bevel, in a radially outer end area of which a distance from said inner surface of said container bottom is greater than in a radially inner area thereof.

8. A sterilization container in accordance with claim 1, wherein:
said sterilization barrier is formed from a Pasteur loop, which is formed from ring webs of said wall area, which mesh with one another axially alternatingly in a radial direction and from said cover plate; and
said locking groove is interrupted by a plurality of recesses, whose number and arrangement correspond to a number and arrangement of said locking elements, and said recesses are open, beginning from said locking groove, towards a wall area of said container cover.

9. A sterilization container in accordance with claim 8, wherein:
said cover plate is rotatable relative to said wall area of said container cover;
said recesses can be caused to overlap said locking elements arranged in the peripheral area of said cover plate and be disengaged from said locking groove by correspondingly setting a relative angular position of said cover plate in relation to said wall area.

10. A sterilization container in accordance with claim 9, further comprising marks provided in the peripheral area of said cover plate on said cover and in an edge area of said cover plate, said marks being arranged radially aligned with one another if said locking elements are located in the peripheral area of the respective associated recess.

11. A sterilization container in accordance with claim 1, wherein said wall area has a central mounting pin, which projects towards said cover plate and on which said cover plate is received in the mounted state with a mounting hole concentrically with said ring segments in said wall area, which said ring segments are arranged on the circumference.

12. A sterilization container in accordance with claim 1, wherein said distance between adjacent locking elements is always selected to be such that said cover plate can be grasped manually between adjacent locking elements on the circumference of said cover plate.

13. A sterilization container comprising:
a lower part;
a removable container cover, said lower part and said container cover, in a closed state, forming a closed airtight sterilization space, a wall area of said container cover having ventilating openings, through which an exchange of air takes place between said sterilization space and the environment in said closed state and said wall area having ring segments integrally connected thereto, said ring segments projecting axially beyond said wall area, each of said ring segments having a mounting hole extending at a right angle to said cover plate, each of said ring segments defining a radial mounting opening, said radial mounting opening being in communication with said mounting hole;
a cover plate comprising a round disk with a peripheral ring wall having an outer peripheral locking groove, said wall area and said cover plate defining a sterilization barrier in the area of said ventilating openings, which brings about sterilization of air entering said sterilization space through said ventilation openings; and
a spring-loaded snap-in or locking connection with a plurality of locking elements arranged in a peripheral area of said cover plate, said locking groove detachably engaging said locking elements, each of said locking elements being arranged stationarily as a separate assembly unit in a corresponding said mounting hole, each of said locking elements comprising a cylindrical or near cylindrical housing block, which is provided with a transversely extending radial hole, in which a locking ball is arranged, which partially projects radially from said housing block and meshes with said locking groove in the mounted state.

14. A sterilization container in accordance with claim 13, wherein:
said cover plate is arranged between said wall area and said container cover; and
said locking ball is held elastically and non-rigidly in a meshed position by an axial compression spring arranged in said radial hole.

15. A sterilization container in accordance with claim 14, further comprising:

a pin, wherein said radial hole in the area of the partially radially projecting locking ball has an inwardly directed stop web, by which a maximum radial projection of said locking ball is established, each of said ring segments comprising an inner ring segment surface, said inner ring segment surface defining an inner ring segment groove, said housing block of each of said locking elements having an outer housing block surface, said outer housing block surface defining an outer housing groove, said inner ring segment groove and said outer housing groove defining a pin receiving groove, at least a portion of said pin being arranged in said pin receiving groove, wherein said housing block is connected to said wall area via at least said pin.

16. A sterilization container in accordance with claim 14, wherein said radial hole of said housing block is provided in an end area located opposite said locking ball with a closing plate, said closing plate being received stationarily in a milled area of said housing block and at which said axial compression spring is axially supported.

17. A sterilization container in accordance with claim 13, further comprising:
   a filter blade covering said ventilating openings on an inside thereof, said filter blade being provided between said cover plate and said wall area of said container cover, wherein
   said locking connection between said cover plate and said wall area brings about a clamping force, with which said filter blade is pressed against said wall area of said container cover.

18. A sterilization container in accordance with claim 13, wherein:
   said cover plate has a radially projecting grip part, which is arranged in amounted state between two adjacent ring segments of said cover plate; and
   said grip part is at a distance from an inner surface of said cover wall of said container cover.

19. A sterilization container in accordance with claim 13, further comprising:
   a Pasteur loop forming a part of said sterilization barrier, said Pasteur loop comprising ring webs of said wall area, which mesh with one another axially alternatingly in a radial direction and from said cover plate; and
   said locking groove is interrupted by a plurality of recesses, whose number and arrangement correspond to a number and arrangement of said locking elements, and said recesses are open, beginning from said locking groove, towards a wall area of said container cover.

20. A sterilization container in accordance with claim 19, wherein:
   said cover plate is rotatable relative to said wall area of said container cover
   said recesses can be caused to overlap said locking elements arranged in the peripheral area of said cover plate and be disengaged from said locking groove by correspondingly setting a relative angular position of said cover plate in relation to said wall area.

* * * * *